United States Patent [19]
Atkinson et al.

[11] Patent Number: 5,608,170
[45] Date of Patent: Mar. 4, 1997

[54] FLOW MEASUREMENT SYSTEM

[75] Inventors: David I. H. Atkinson, Clamart, France; Ian C. Walton, Tulsa, Okla.; Bernard J. P. Glotin, S.-Maur-des-Fosses; Gérard Segeral, Gif-sur-Yvette, both of France

[73] Assignee: Schlumberger Technology Corporation, Houston, Tex.

[21] Appl. No.: 290,828

[22] PCT Filed: Feb. 22, 1993

[86] PCT No.: PCT/GB93/00369

§ 371 Date: Nov. 16, 1994

§ 102(e) Date: Nov. 16, 1994

[87] PCT Pub. No.: WO93/17305

PCT Pub. Date: Sep. 2, 1993

[30] Foreign Application Priority Data

Feb. 21, 1992 [GB] United Kingdom ............... 9203760

[51] Int. Cl.$^6$ ........................................................ G01F 1/74
[52] U.S. Cl. .................................................................. 73/861.04
[58] Field of Search .............................................. 73/861.04

[56] References Cited

U.S. PATENT DOCUMENTS

| | | | |
|---|---|---|---|
| 3,834,227 | 9/1974 | Patterson et al. | 73/155 |
| 3,908,761 | 9/1975 | Patterson et al. | 166/250 |
| 3,926,050 | 12/1975 | Turner et al. | 73/205 D |
| 4,282,760 | 8/1981 | Pitts, Jr. et al. | 73/861.04 |
| 4,312,234 | 1/1982 | Rhodes et al. | 73/861.04 |
| 4,856,344 | 8/1989 | Hunt | 73/861.04 |
| 5,239,862 | 8/1993 | Atkinson | 73/64.44 |

FOREIGN PATENT DOCUMENTS

| | | |
|---|---|---|
| 478044 | 4/1992 | European Pat. Off. |
| 1272152 | 4/1972 | United Kingdom. |
| 1461537 | 1/1977 | United Kingdom. |

OTHER PUBLICATIONS

National Engineering Laboratory, Paper 6.2, Oct. 23–25, 1990, "Simple Full–Bore Water–Cut Measurement Technique", D. Brown et al.

The Institute of Physics, vol. 18, Feb. 18, 1985, "Rapid Communication— Non–intrusive Three–Component Ratio Measurement Using An Impedance Sensor", Eivind Dykesteen, et al.

*Primary Examiner*—Richard Chilcot
*Assistant Examiner*—Jewel Artis
*Attorney, Agent, or Firm*—John E. Vick, Jr.

[57] ABSTRACT

Apparatus for measuring multiphase fluid flows comprising first and second sections each comprising a flow passage having means for making a dynamic pressure measurement on the multiphase fluid flow therethrough, the geometry of the first and second sections differing so as to affect a relationship between void fraction and velocity for the phases in a known manner. The difference in geometry between the two sections can be in the area of the flow passages or in the direction of flow relation to gravity. A method of measuring multiphase flows comprising the steps of:

a) directing the flow through a first flow passage including means for making a dynamic pressure measurement;

b) measuring a pressure drop across said means;

c) directing the flow through a second flow passage including means for making a dynamic pressure measurement;

d) measuring a pressure drop across said means; and e) calculating the composition and flow rates of the phases from the measured pressure drops.

The method optionally includes the further steps of directing the flow through a pair of passages and f) intermittently isolating one or other of said pair of passages to prevent flow therethrough;

g) measuring at least one property of the fluid as the phases separate in the isolated passage.

10 Claims, 3 Drawing Sheets

FLOW MEASUREMENT SYSTEM

BACKGROUND OF THE INVENTION

The present invention relates to a system for measuring flows of fluids which comprise more than one discrete phase. In particular, the invention relates to a system for measuring two or three phase flows from hydrocarbon wells.

The problems associated with measuring the flow rate of a multiphase fluid are well known. Techniques which are applicable to single phase flows, such as impeller systems and the like, have been shown to be highly inaccurate in multiphase flows, and often more than one measurement must be made to enable an accurate measurement of the volumetric flow rates of the various phases. In the oil and gas industry the measurement of multiphase flow is routinely encountered and in the case of producing wells it is common for the produced fluid to comprise a mixture of oil, water and often gas as well. Since it is important to determine the volumetric flow rates of the individual phases at times throughout the life of the well to determine if any remedial action is required to improve or restore the productivity of the well and to assess exactly how much oil is being produced, various methods of flow measurement have been proposed Typically, the fluids are fed to separators and the volumes of each phase determined separately. However, this requires a large installation and is not able to give an instantaneous determination of the current production from a well. A typical surface system fluid from the well head passes through a choke manifold which can either be a separate system or part of a heater-steam exchange. The fluid is then divided into individual phases with a three phase separation and the flow rates measured at separation temperature and pressure. Samples of the fluids at these conditions are taken, the oil sample being used to determine the oil "shrinkage factor". The oil phase is passed to a gauge tank at atmospheric pressure which permits calibration of the flow meters and atmospheric oil samples to be taken.

Systems for measuring multiphase flow are described in U.S. Pat. No. 4,856,344. The system described in this patent comprises a gradio-venturi flow meter arrangement which, by means of differential pressure measurements along its length, provides information concerning the flow rates of the phases. A homogenizer comprising a step discontinuity in the pipe diameter is provided upstream of the measurement section in order to ensure that the separate phases are well mixed in the measurement section.

In GB 1,272,152, GB 1,461,537 and in the Paper 6.2 North Sea Flow Measurement Workshop 1990, National Engineering Laboratory, Glasgow entitled "Simple Full-Bore Water-Cut Measurement Technique" by D. Brown and J. J. der Boer, there are proposed various systems for making measurements on multiphase flows. In each case, the apparatus has the form of an inverted "U", and a series of pressure measurements are made at differing heights in each leg of the "U" and compared to determine some parameter of the flow. Since none of the measurements relate to dynamic pressure changes, determination of the flow rates of the phases is not possible from the pressure measurement alone.

Measurement of the complex impedance of a multiphase fluid can also provide information on the flow rates, but calibration of the meters is important in view of the potentially large effects of relatively small changes in the composition of the fluid phases. In our co-pending European patent application no. 91202327.2 there is described a system in which the flow is directed through a pair of parallel instrumented flow passages. Periodically, one or other of the passages is isolated from the flow and the fluid therein is allowed to separate under the effect of gravity. Measurements are made on the separating mixture at different locations along the passage such that the concentration of each phase and its contribution to the complex impedance can be determined.

SUMMARY OF THE INVENTION

It is an object of the present invention to provide a system in which the volumetric flow rates of the different phases in a multiphase flow can be determined substantially continuously.

A first aspect of the present invention provides an apparatus for measuring multiphase fluid flows comprising first and second sections each comprising a flow passage having pressure measurement means so as to measure the multiphase fluid flow therethrough, the geometry of the first and second sections differing so as to affect a relationship between void fraction and velocity for the phases; characterized in that the pressure measurement means comprise dynamic pressure measurement means and in that the geometry of the first and second sections differs in respect of the area of the flow passages and/or the direction of flow in relation to gravity.

The difference in geometry between the two sections can be in the area of the flow passages or in the direction of flow relation to gravity. In the first case, the second section can have a smaller flowing area than the first. In the second case, the first section can have an upward component and the second section a downward component. Conveniently, the sections are substantially vertical such that flow is up in the first section and down in the second section.

The means for making a dynamic pressure measurement can comprise any suitable device for measuring a pressure drop when the flow passes through the device and might also be known as differential pressure devices. Dynamic pressure measurement means include gradio-venturi devices, orifice plates, nozzles, Bernoulli devices and the like.

In one embodiment of the invention, one of the sections comprises a single flow passage and the other section comprises a pair of passages and includes means to isolate one or other of the pair of passages and means to measure at least one property of the fluid in the isolated passage as the phases separate.

It is preferred that both the first and second sections comprise pairs of passages and include means to isolate one or other of the respective pair of passages and means to measure at least one property of the fluid in the isolated passages as the phases separate.

The means to measure at least one property of the fluid can comprise one or more impedance meters.

The present invention also provides a method of measuring multiphase flows comprising the steps of:

a) directing the flow through a first flow passage including means for making a dynamic pressure measurement;

b) measuring a pressure drop across said means;

c) directing the flow through a second flow passage including means for making a dynamic pressure measurement;

d) measuring a pressure drop across said means; and e) calculating the composition and flow rates of the phases from the measured pressure drops.

One embodiment of the method includes the further steps of directing the flow through a pair of passages and f) intermittently isolating one or other of said pair of passages to prevent flow therethrough;

g) measuring at least one property of the fluid as the phases separate in the isolated passage.

In this embodiment of the method according to the invention, the flow can be directed upwardly through a substantially vertical passage in which the pressure drop is measured, and downwardly through a pair of substantially vertical flow passages in which the pressure drop is measured and which are isolated and measured as before. Alternatively, the flow is directed upwardly through a first pair of passages and downwardly through a second pair of passages, one or other passage of each pair being isolated and measured as before.

It is preferred that each flow passage includes a plurality of devices for making measurements on the flowing fluid. The passages can all be substantially identical except for vertical orientation. It is preferred that each passage of a pair is substantially identical and includes the same devices for monitoring the fluid as the phases separate.

The devices for measuring the parameters of the flowing fluid typically include differential pressure devices, gradio-venturi devices and impedance meters. The devices for measuring the properties of the fluid as the phases separate typically comprise impedance meters. Other suitable devices are nozzles, orifice plates and other Bernouilli devices.

BRIEF DESCRIPTION OF THE DRAWING

The present invention will now be described by way of example, with reference to the accompanying drawings, in which.

DESCRIPTION OF THE PREFERRED EMBODIMENT

Figure 1:
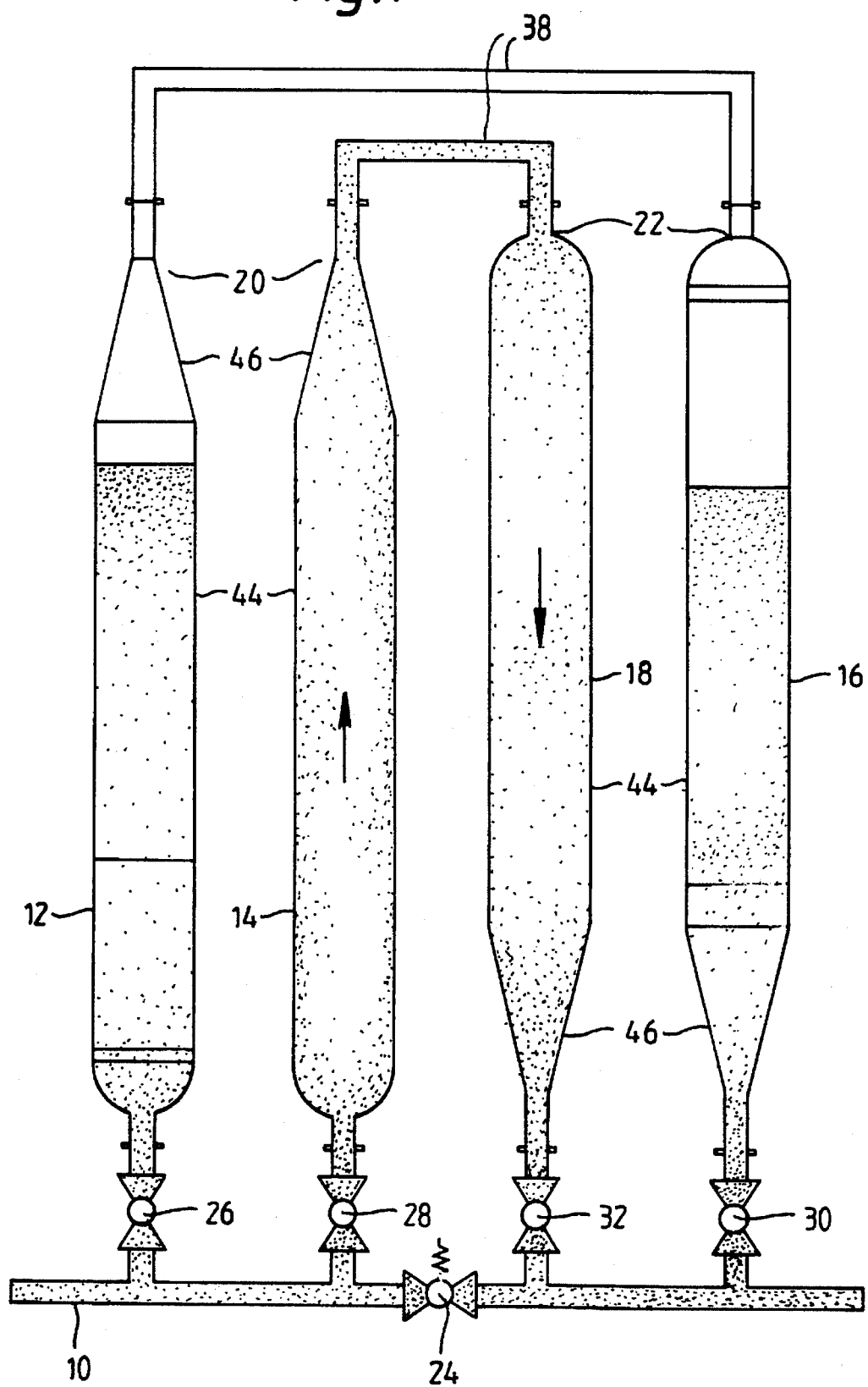
FIG. 1 shows a diagrammatic view of an apparatus according to one embodiment of the invention.

One embodiment of an apparatus according to an aspect of the present invention is shown in FIG. 1 and comprises part of a surface measurement system for a hydrocarbon well (not shown). The measuring apparatus is connected to the well by means of a pipe 10. A first section of the apparatus comprises a pair of substantially vertical flow passages 12, 14 which are arranged to receive the multiphase fluid from the pipe 10 via inlet valves 26, 28 and direct it upwards. The second section of the apparatus comprises two further vertical flow passages 16, 18 which are essentially the same as those in the first section but are inverted and arranged to direct flow downwards to return to the pipe 10 via outlet valves 30, 32. The upper, outlet end 20 of each passage in the first section is connected to the upper, inlet end 22 of a corresponding passage in the second section by means of a connecting pipe 38 which is the same diameter as the pipe 10. A pressure relief valve 24 is provided in the pipe 10 between the inlet valves 26, 28 for the first section and the outlet valves 30, 32 of the second section.

The two test sections are identical mechanically and in terms of instrumentation. The only difference is in their orientation with respect to gravity. Each test section comprises a gradiomanometer section 44 and a fixed venturi 46 with the option of adding a second venturi 40% along the length of the manometer section 44.

The valves 26–32 are arranged such that only one of the passages in the first section and the corresponding passage in the second section is connected to the flowing fluid at any one time, the remaining two passages being isolated from the flowing fluid. Periodically the valves are operated such that the isolated passages are connected to the flow and the previously flowing passages are isolated. Thus at any one time one pair of passages (together forming an inverted 'U' section) is measuring the flowing fluid while the other makes measurements as the phases separate in order to calibrate the sensors with a current sample of the fluid.

An inverted 'U' section has the benefit of different slip velocities in the two 'arms', an increase in the total volume without paying a height penalty, and when the valves are closed and separation of the phases started, the only phase which will go over the 'crest of the U' will be gaseous. The two arms are effectively separate as far as the liquid phases are concerned as long as the volume of fluid in the crest is small compared with the total test section volume. The liquid volume fractions measured in the two arms will therefore reflect the concentration in that arm; if the slip in the arms are different, then the concentrations will also be different.

Figure 2:
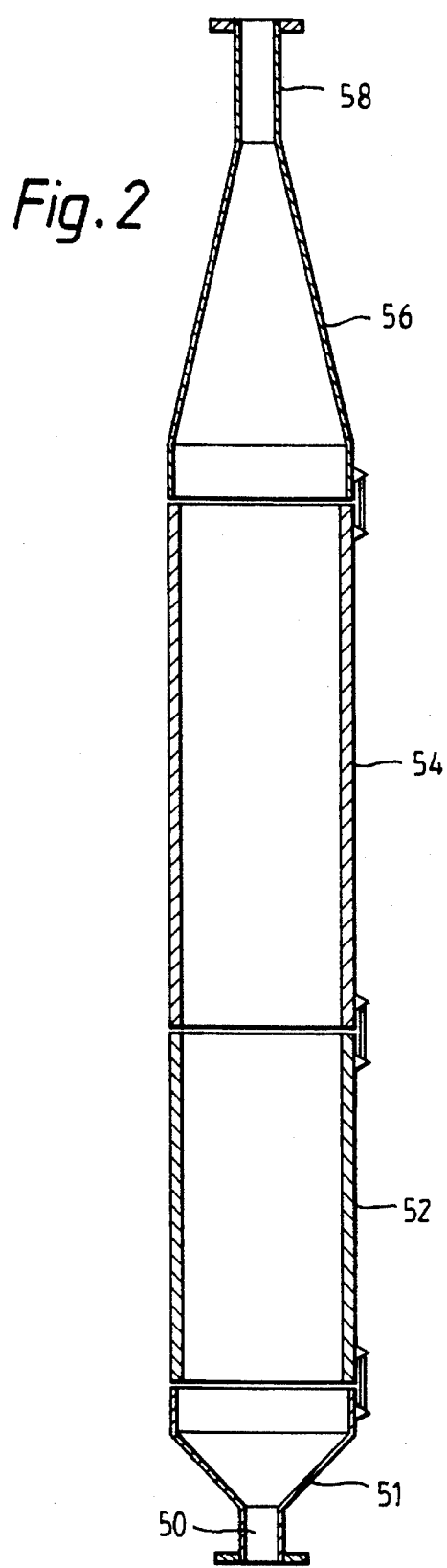
FIG. 2 shows a detailed view of a flow passage as shown in FIG. 1.

FIG. 2 shows a detailed view of a flow passage. This consists of a valve (not shown) in a nominal 60 mm bore pipe 50 with an expansion 51 to a 280 mm bore pipe 52 which comprises the main test section 54 (e.g., gradiomanometer); then a venturi contraction 56 to a 60 mm bore pipe 58. The second test section is of identical design but rotated (i.e., inverted) 180 degrees.

The expansion 51 expands from 60 ram to 280 ram, and has a 90 degree included angle. The expansion is designed to create a mixing of the fluid. The ideal total included angle is 180 degrees, but this would create a trap for solids or gas depending on orientation.

The 280 mm bore pipe 52 has a relatively large diameter which reduces the flow velocities in turn which means a gradiomanometer will not require a friction correction and the total volume of the 'U' section is maximized with minimum height.

The venturi section 56 comprises a straight contraction with a 21 degree included angle. The contraction ratio is the largest that can be achieved with the pipes used; smaller contraction ratios can be obtained by adding further venturi sections.

The Table below details various parameters for one Test Section:

|  | Volume enclosed m³ | Reynolds No. Max. Liquid | Liq. Vel. Max. m/s | Pressure Work/Test bar |
| --- | --- | --- | --- | --- |
| 280 mm Pipe | 0.09 | 100000 | 0.4 | 11/110 |
| Reducer (90 deg) | 0.009 | 430000 | 9.0 | 47/82 Sch. 5 |
| Reducer (21 deg) | 0.02 | 430000 | 9.0 | 47/82 Sch. 5 |
| TOTAL | 0.119 | | | |

The volume concentration is determined by measuring the heights of the separated phases; because of 'blind' volumes at the top and bottom of the test section there are minimum and maximum values of the concentration which can be observed. These are tabulated below:

|  | Outer 'U' section(*) | Inner 'U' section(**) |
| --- | --- | --- |
| Total Volume m³ | 0.243 | 0.240 |
| Minimum Concentration | 0.07 | 0.08 |
| Maximum Concentration | 0.81 | 0.83 |

(*)assuming a 60 mm pipe volume of 0.0048 m³ joining the sections
(**)assuming a 60 mm pipe volume of 0.0023 m³ joining the sections If the boundary between two phases is sited between the pressure tappings across the venturi section, then the boundary position can be determined from the measurement of the hydrostatic head and knowledge of the pure phase densities. Differences in the slip velocities between the two legs will result in the phase boundaries being at different heights in the legs after separation.

Both legs of the 'U' section will have identical transducers, across the venturi and along the test section.

The differential pressure $\Delta P_g$, measured by the gradiomanometer is given by:

$$\Delta p.g = \rho.g.h + Fm$$

$$Fm = 2.f.\rho.v^2.h/D$$

f=function of Reynolds number f typically=0.006 for single phase, smooth pipes $$\rho = c(1).\rho(1) + c(2).\rho(2) + c(3).\rho(3)$$

$$c(1) + c(2) + c(3) = 1$$

where $\rho$=mixture density $\rho(i)$ =density of phase i g=acceleration due to gravity h=distance between pressure tappings V=velocity f=friction factor D=pipe internal diameter c(i)=volume concentration of phase i Hence, a measurement of $\Delta P_g$ and knowledge of the frictional pressure drop Fm, allows the mixture density to be measured. For two phase flows, knowledge of the pure phase densities allows the phase concentrations to be calculated but this is not the case with three phase flows. The frictional pressure drop for two phase flows is typically calculated from a single phase calibration. However, this approach can introduce significant errors in the calculation of the void fraction. The calculation of the frictional pressure drop for three phase flows is considered to be complicated. In order to minimize the frictional pressure drop term the fluid velocity needs to be minimized and the pipe diameter maximized. If the frictional pressure drop, is ignored and the mixture density is calculated from the measured pressure drop, then the fractional error in the density is given by:

fractional density error=$2.f.v^2/D/g$ for f=0.006

D=0.28 m v=1m/s then the fractional density error=0.004 (i.e., 0.4%).

for f=0.006

D=0.06 m v=9m/s then the fractional density error=1.7 (i.e., 170%).

In vertical two-phase flow in a pipe, a single measurement of the pressure difference between two points provides insufficient information with which to determine the three unknown quantities $\alpha$: void fraction $Q_1$: mass flowrate of phase 1

$Q_2$: mass flowrate of phase 2.

The gradio-venturi flow meter described above in relation to FIG. 1 incorporates two differential pressure measurements, one across a straight section of pipe (the gradio) and one across a contraction (the venturi). A mathematical model of two-phase flow in the venturi is needed to relate the measured pressure differential to the unknown quantities $\alpha$, $Q_1$, $Q_2$. Even so, the two measurements are insufficient to determine the three unknown quantities and an empirical relation (such as a relative or slip velocity) must be added to complete the formulation.

In the apparatus shown in FIG. 1, there are two gradio-venturi devices, one in which the fluids flow vertically upwards and one in which they flow vertically downwards. On the assumption that the mass flowrates of each phase are unchanged across the two legs of the apparatus, there are now four unknown quantities:

$\alpha_u$: volume fraction of phase 1 in the up leg $\alpha_d$: volume fraction of phase 1 in the down leg $Q_1$: mass flowrate of phase 1

$Q_2$: mass flowrate of phase 2.

The total of four differential pressure measurements is now sufficient to determine all the unknown quantities without recourse to an external empirical relation.

The four unknown quantities are related to (the absolute values of) the four differential pressure measurements $\Delta \rho_{gu}$: pressure differential across the gradio in the up leg $\Delta \rho_{vu}$: pressure differential across the venturi in the up leg $\Delta \rho_{gd}$: pressure differential across the gradio in the down leg $\Delta \rho_{vd}$: pressure differential across the venturi in the down leg by the following equations.

By conservation of momentum in the gradio sections $$\frac{\Delta \rho_{gu}}{\Delta L} = \alpha_u g \Delta \rho + \frac{2fpQ^2}{A^2 D}$$

$$\frac{\Delta \rho_{gd}}{\Delta L} = \alpha_d g \Delta \rho + \frac{2fpQ^2}{A^2 D}$$

Here, $\Delta \rho$ is the absolute value of the fluids' density difference, $f$ is a (two-phase) friction factor, $\rho$ is a mixture density defined by $\rho = \alpha \rho_1 + (1-\alpha)\rho_2$, $\Delta L$ is the separation of the pressure tappings, A is the cross-sectional area and D is the diameter of the pipe. Q is a mixture volumetric flowrate.

The equations which describe two-phase flow in the venturi sections are developed from the equations of conservation of mass and momentum. The development is similar to that for single-phase flow through a venturi, but is appropriately generalized to two-phase flow.

In the up leg of the UUC a mixture flowrate, $Q_m$, is related to the pressure differential by $$Q_m = CEA_v(2\rho(\Delta \rho_{vu} - \Delta \rho_g \Delta L)^{1/2}),$$

where C is the discharge coefficient, E is a geometric factor defined by $E=(1-\beta^1)^{-1/2}, \beta=d_v/d_g$ $D_v/D_g$ is the concentration ratio of the venturi and $A_v$ is the downstream cross-sectional area (at discharge). The mass flowrate of the mixture is defined by $$Q_m^2 = \rho \left( \frac{Q_1^2}{\alpha_v \rho_1} + \frac{Q_2^2}{(1-\alpha_v)\rho_2} \right)$$

A similar set of equations holds for the down leg.

To determine the superficial velocity of the discontinuous phase requires an estimate of the slippage between the two phases. Hunt *Int. J. Multiphase Flow* Vol.14 No. 5 pp. 587–606, 1988 describes a method based on empirical correlations of Zuber 1964 *Chem. Eng. Sci.*19, p. 897; these correlations involve two constants and a single bubble rise velocity. An Harmarthy (1960 *ACILE Journal*6, 281) relationship for the single bubble velocity is proposed involving one constant and a surface tension. Hence three numerical 'constants' are required together with a knowledge of the surface tension.

In three phase flow the above relationships can be used; if there is no slip between the liquid phases, then the fluid can be considered as two phase (liquid+gas). This requires good mixing of the liquid phases. In the apparatus shown, a Venturi is positioned in each passage such that there is one with the flow direction against gravity, the other in the direction of gravity. This provides the potential for two different slip velocities in the two branches. This will not provide enough information to determine the four superficial velocities (gas and liquid per branch) but conservation of mass in the two branches allows a solution to the discontinuous phase superficial velocities. It is possible to determine Zuber type slippage relationships from this phenomenon.

In the system there are several calibration constants, i.e., the discharge coefficient c of the venturi/orifice meters, the friction factor f in the gradio-manometers. With suitable design (mainly physical dimensions) the friction factors (or more correctly the Fanning Factors) can be minimized and be zero for certain flow rate ranges. The discharge coefficient (typically approximately 1 for a venturi and 0.6 for an orifice plate) requires single phase calibration over the operational flow ranges (unless the design is such that the coefficient can be calculated from the dimensions of the device).

There are two possibilities which are partial solutions to this problem: 1) with single phase fluid (e.g., water or oil) each of the gradio-venturi combinations will give the same results for mass flow rate and density (i.e., in single phase flow a gradio-venturi system provides enough information for the density and mass flow rate to be determined). This can be used as a check but it is not a true in-line calibration; 2) with a stock tank or other calibrated reservoir and single phase fluid flowing, the density and mass flow rate can be independently measured; these data can be used to determine the flow meter constants (discharge coefficient and friction factor)for each leg. This can be used as either an in-line calibration or a check of laboratory calibration.

A major disadvantage of the venturi is the turn-down ratio on pressure. Therefore for different flow conditions and a given differential pressure measurement range, different contraction ratios can be used to accommodate the turn-down problem. Alternatively a variable range DP transmitter could be used. The use of orifice plates in the place of the venturi meters has a number of advantages. Venturi meters do not have a large dynamic flow range, so to cover a large range, the meter has to be either changed (i.e., removed and replaced with the line pressure being dropped to atmospheric), or there has to be a number of venturi meters in series. It is standard practice in oil-field applications to install orifice plates in orifice plate changers which allow the plates to be changed without dropping the line pressure to atmospheric. Furthermore, the physical length of an orifice plate is very small compared to a venturi meter and is generally of lower cost and weight.

Because in the apparatus continuous measurements are made in the passages in which fluid is flowing, the isolated section provides a 'sample' which can be used for in-line calibration. Periodically the 'sample' section becomes the flowing section and vice versa. The sample in the closed section will be representative of that flowing in the line at the sampling time if the valves close at an infinite rate. Fluid entering or leaving the section while the valves are closing will not necessarily be representative of that flowing in the main pipeline. The total volume of fluid that enters and leaves during valve closure can be used as a measure of the upper limit on the degree of non-representation of the isolated sample. The fractional error e, is given by $$e = \frac{\text{total volume entering} + \text{leaving during valve closure}}{\text{total sample volume}}$$

$$e = \frac{2 \cdot v(i) \cdot A(t) dt}{V tot}$$

where v(i)=fluid velocity in the valve section

A(t)=cross sectional area presented for the fluid to flow through during valve closure or opening Tc=time for the valve to change from totally open to closed Vtot=total volume enclosed in the test section The valves should have the following properties:

a) Two state—open/closed, b) when closed must be gas tight, c) capable of withstanding solids in the flow, d) low erosion potential, e) when open a low pressure drop is desirable, f) when closed the pressure across the valve will be small, g) closing time=opening time, and h) time to go from open to closed to be as small as possible.

A "ball valve" will satisfy the majority of these requirements.

Measurement of the fluid dielectric constant and resistivity (i.e., the complex impedance) allows a determination of the volume concentrations of the phases, given the electrical properties of the pure phases and a model of the fluid impedance (see Dykesteen et al *J. Phys.* E18 1985). There are a number of potential problems with this approach, a solution to some of which is an in-line calibration method of the type described in our co pending European application and used generally in the present invention. In this scheme the complex impedance of the flowing fluid is measured and then a sample of the fluid is isolated and the impedance measured at a number of vertical positions in the isolated sample using the same transducers as with the flowing fluid. The impedance is monitored against time while the fluid separates under gravity; at a given position the concentration will vary with time. The pure phase impedance measurements are made when separation is complete. A mathematical model of the phase separation against time permits the calibration of the measurements against concentration. The basic concept is to use time as a 'dummy' variable linking the impedance to concentration. No prior knowledge of the impedance as a function of the pure phases impedances and concentrations is required; the initial mixture concentrations are determined from the separated volume fractions.

With no calibration of an impedance transducer, the output can be used as a 'quality' monitor in combination with other measurements. For example, if, for a given section of the apparatus, the impedance while fluid is flowing is constant, then a function of the pure phases electrical properties, the concentrations and a shape factor is constant between the sample periods. If the concentrations and electrical properties of two consecutive samples are the same then there is reasonable confidence that the concentrations while flowing were constant; it is unlikely that the electrical properties of the pure phases will change on a time scale comparable with the sampling period.

Figure 3:
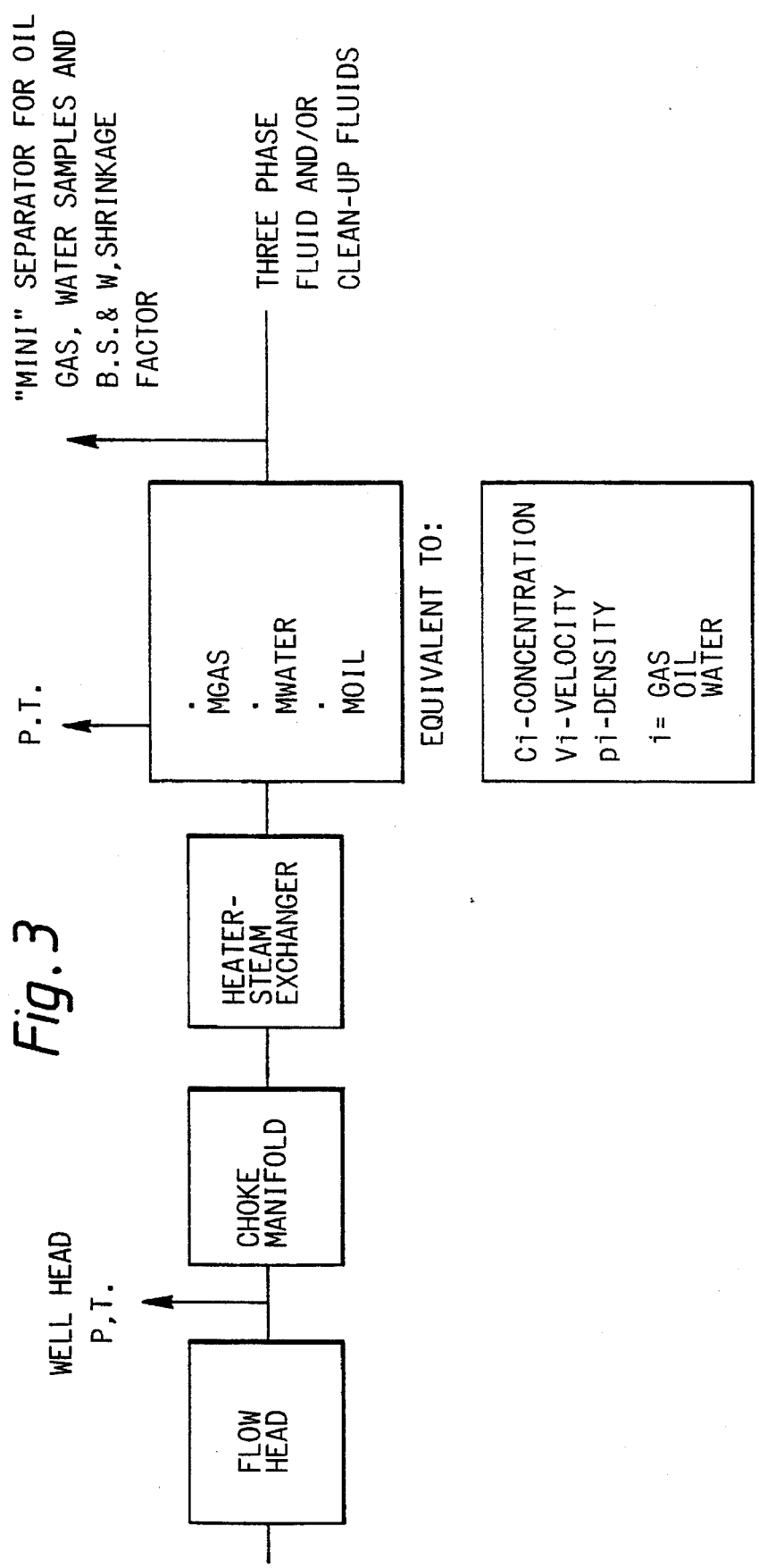
FIG. 3 shows a block diagram of surface testing system incorporating the apparatus.

An impedance transducer could be used in this 'quality' mode to assess whether fluid entering the test section while the valves are closing is representative of the fluid flowing with the valves fully open. This is dependent on the response speed of the transducer relative to the valve closing time. Calibration may allow the degree of non-representation to be assessed. Design of an impedance transducer depends on the dynamic range, which is very large and the relatively small capacitances to be measured; spatial resolution is another factor which is involved in the electrode design. The apparatus of the present invention can be incorporated into a surface testing system as shown in FIG. 3. This is similar to that described above except that in the present case, after the heater-steam exchanger, the flow from the well is passed to an apparatus as described above where the flow measurements are made. The fluids are passed from the apparatus to a separator where samples can be taken as before.

While the above described system relates to well testing, it will be appreciated that the simpler system can be used for continuous well monitoring.

Figure 4:
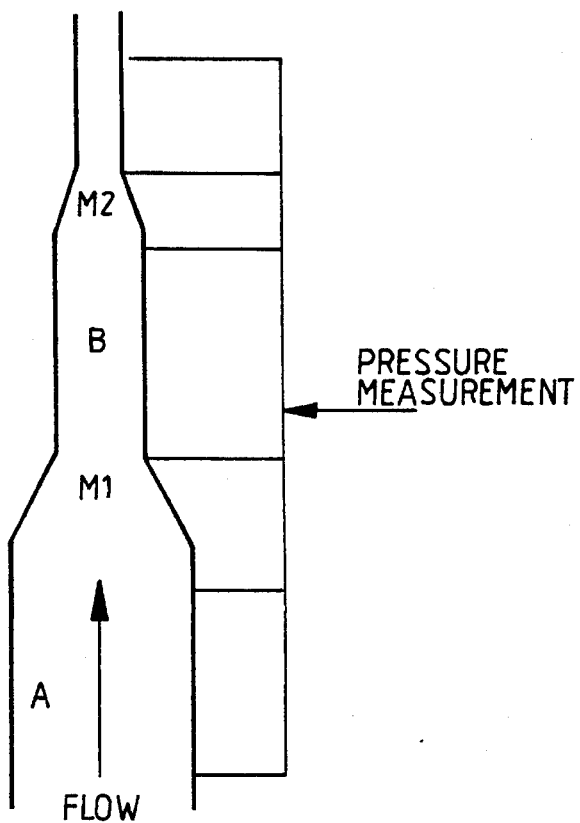
FIG. 4 illustrates a further embodiment of the present invention.

A further embodiment of the invention is shown schematically in FIG. 4. In this case, the device is simply a flow meter with no sampling or in-line calibration provided although this could be achieved in a comparable way to the systems described above. In FIG. 4, the device comprises two measurement sections A, B of different diameters and each including a measuring device $M_1, M_2$ such as a gradioventuri flow meter, orifice plate or the like, which measures substantially the same parameters of the flow in each section. It will be appreciated that while the mass flow in each section is the same, the velocities and pressure drop will be different between the sections allowing the form parameters $\alpha_1, \alpha_2, Q_1, Q_2$ to be derived.

We claim:

1. An apparatus for measuring multiphase fluid flows comprising:

first and second sections each having a respective flow passage, said first and second sections having one of a differing area of flow and a differing direction of flow in relation to gravity so as to affect a relationship between a void fraction and a velocity for the phases; and dynamic pressure measurement means associated with said flow passages for measuring said multiphase fluid flows therethrough.

2. An apparatus as defined in claim 1, wherein said second section has a smaller area of fluid flow than said first section.

3. An apparatus as claimed in claim 1, wherein said sections are substantially vertical, the direction of fluid flow being upwards in said first section and downwards in said second section.

4. An apparatus as defined in claim 1, wherein one of said sections comprises a pair of flow passages, means for isolating one of said flow passages of said pair, and means for measuring a further property of said fluid as the phases separate in said isolated passage.

5. An apparatus as defined in claim 4, wherein each of said sections comprises a pair of flow passages, said means for respectively isolating one of said flow passages of each pair, and means for measuring a further property of said fluid as the phases separate in said isolated passages.

6. An apparatus as claimed in claim 4, wherein said means for measuring comprises an impedance meter.

7. A method of measuring multiphase fluid flow, comprising the steps of:

a) directing said flow through a first flow passage having first dynamic pressure measurement means;

b) measuring a pressure drop across said first dynamic pressure measurement means;

c) directing said flow through a second flow passage having a different geometry to said first flow passage, said second flow passage including second dynamic pressure measurement means;

d) measuring a pressure drop across said second dynamic pressure measurement means; and e) calculating a composition and a flow rate of the phases from said pressure drops of said measuring steps.

8. A method as defined in claim 7, wherein one of said directing steps includes directing said flow through a pair of flow passages; and further comprising the steps of:

f) isolating intermittently one of said flow passages of said pair to prevent said flow therethrough; and g) measuring a further property of said fluid as said phases separate in said isolated passage.

9. A method as defined in claim 8, further comprising the step of arranging each of said passages to be substantially vertical; and wherein said directing step (a) includes directing said flow in an upward direction to perform said measuring step (b), said directing step (c) includes directing said flow in a downward direction through one of said pair of said second flow passages to perform said measuring step (d), and isolating the other one of said pair of said second flow passages to perform said measuring step (g).

10. A method as defined in claim 8, wherein said directing step (a) includes directing said flow in an upward direction through a first pair of passages, said directing step (c) includes directing said flow in a downward direction through a second pair of passages, and said isolating step (f) includes isolating one of each said passage of each said pair to perform said measuring step (g).

* * * * *